United States Patent
Cheng et al.

(10) Patent No.: US 10,105,186 B2
(45) Date of Patent: Oct. 23, 2018

(54) VIRTUAL RIGID BODY OPTICAL TRACKING SYSTEM AND METHOD

(71) Applicant: The Johns Hopkins University, Baltimore, MD (US)

(72) Inventors: Alexis Cheng, Baltimore, MD (US); Emad M. Boctor, Baltimore, MD (US); Xiaoyu Guo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 515 days.

(21) Appl. No.: 14/734,778

(22) Filed: Jun. 9, 2015

(65) Prior Publication Data

US 2016/0000516 A1    Jan. 7, 2016

Related U.S. Application Data

(60) Provisional application No. 62/009,777, filed on Jun. 9, 2014.

(51) Int. Cl.
| | | |
|---|---|---|
| *A61B 5/05* | (2006.01) | |
| *A61B 34/20* | (2016.01) | |
| *A61B 10/04* | (2006.01) | |
| *A61B 17/34* | (2006.01) | |
| *A61B 18/00* | (2006.01) | |
| *A61M 25/01* | (2006.01) | |

(Continued)

(52) U.S. Cl.
CPC ............. *A61B 34/20* (2016.02); *A61B 90/50* (2016.02); *A61B 2010/045* (2013.01); *A61B 2017/3413* (2013.01); *A61B 2018/00577* (2013.01); *A61B 2034/2055* (2016.02); *A61B 2034/2057* (2016.02); *A61B 2034/2065* (2016.02); *A61B 2090/378* (2016.02); *A61B 2090/3945* (2016.02); *A61B 2090/3983* (2016.02); *A61M 2025/0166* (2013.01)

(58) Field of Classification Search
CPC .............................. A61B 5/06; A61B 19/5244
See application file for complete search history.

(56) References Cited

U.S. PATENT DOCUMENTS

| | | |
|---|---|---|
| 6,503,195 B1 | 1/2003 | Keller et al. |
| 8,638,446 B2 | 1/2014 | Briggs |
| 2002/0016541 A1 | 2/2002 | Glossop |

(Continued)

FOREIGN PATENT DOCUMENTS

EP    2438880 A1    4/2012

OTHER PUBLICATIONS

International Search Report and Written Opinion in International Application No. PCT/US2015/034936 dated Aug. 31, 2015.

(Continued)

*Primary Examiner* — Hien Nguyen
(74) *Attorney, Agent, or Firm* — Harrity & Harrity, LLP

(57) ABSTRACT

A virtual rigid body optical tracking system includes a virtual rigid body generator for projecting a virtual rigid body, wherein the virtual rigid body forms a pattern of light on a surface. The virtual rigid body optical tracking system includes an optical detection system for detecting the pattern of light, and a data processing system in communication with the optical detection system. The data processing system is configured to determine a position of the virtual rigid body generator based on the detected pattern of light.

20 Claims, 13 Drawing Sheets

(51) Int. Cl.
*A61B 90/00* (2016.01)
*A61B 90/50* (2016.01)

(56) References Cited

U.S. PATENT DOCUMENTS

| | | | | |
|---|---|---|---|---|
| 2008/0312533 | A1* | 12/2008 | Balberg | A61B 5/14546 600/437 |
| 2011/0040175 | A1 | 2/2011 | Shahidi | |
| 2013/0006120 | A1 | 1/2013 | Druse et al. | |

OTHER PUBLICATIONS

Arun et al (1987) Least-Squares Fitting of Two 3-D Point Sets. Pattern Analysis and Machine Intelligence, IEEE Transactions on (vol. PAMI-9 , Issue: 5 ).
Boctor et al (2004) A Novel Closed Form Solution for Ultrasound Calibration. IEEE Symposium on Biomedical Imaging 527-530.
Byrd et al (1988) Approximate solution of the trust region problem by minimization over two-dimensional subspaces. Mathematical Programming Jan. 1988, vol. 40, Issue 1-3, pp. 247-263.
Cheng et al (2014) Concurrent photo acoustic markers for direct three-dimensional ultrasound to video registration. Proc SPIE 8943-89435J.
Espiau et al (1992) A new approach to visual serving in robotics. IEEE Transactions on Robotics and Automation 8(3):313-326.
Guo et al (2015) Integrated Active Ultrasound Systems for Medical Interventions. Dissertation Defense, Abstract only.
Hartley et al (1997) Triangulation. Computer Vision and Image Understanding 68(2):146-157.
Horn et al (1987) Closed-form solution of absolute orientation using unit quaternions. J Opt Soc Am A 4(4):629-642.
Krupa et al (2009) Real-time Motion Stabilization with B-Mode Ultrasound Using Image Speckle Information and Visual Serving the International Journal of Robotics Research 28(10):1334-1354.
Liu et al (1998) A New Calibration method in 3D Ultrasonic Imaging System. IEEE Engineering in Medicine and Biology Society 20(2):839-841.
Marquardt et al (1963) An Algorithm for Least-Squares Estimation of Nonlinear Parameters. Siam J. Appl Math 11:431-441.
McIlroy et al (2012) Kinectrack: Agile 6-DoF tracking using a projected dot pattern. IEEE International Symposium on Mixed and Augmented Reality 23-29.
Salvi et al (2004) Pattern codification strategies in structured light systems. Pattern Recognition 37(4):827-849.
Scharstein et al (2003) High-Accuracy Stereo Depth Maps Using Structured Light. IEEE Proc. of Computer Vision and Pattern Recognition 195-202.
West et al (2004) Designing optically tracked instruments for image-guided surgery. IEEE Trans Med Imaging. May 2004;23(5):533-45.
Wienss et al (2006) Sceptre: an infrared laser tracking system for virtual environments. VRST '06 Proceedings of the ACM symposium on Virtual reality software and technology pp. 45-50.
Zhang et al (2000) A flexible new technique for camera calibration. IEEE Transactions on Pattern Analysis and Machine Intelligence 22(11):1330-1334.
Levenberg, K., "A Method for the Solution of Certain Non-Linear Problems in Least Squares," Quart. Appl. Math. vol. 2, pp. 164-168, 1944.

* cited by examiner

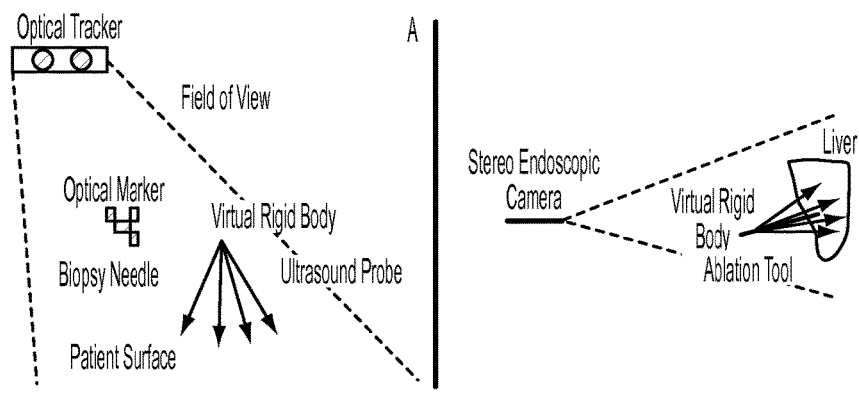
FIG. 3A                    FIG. 3B
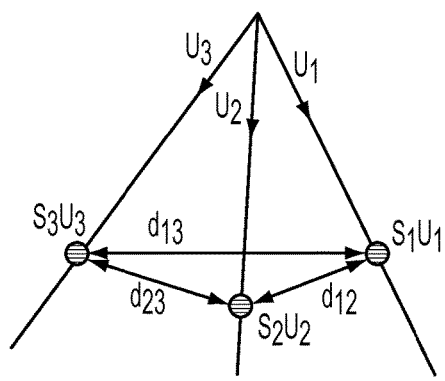    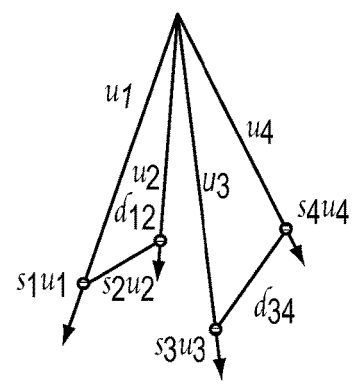
FIG. 4A                    FIG. 4B

VIRTUAL RIGID BODY OPTICAL TRACKING SYSTEM AND METHOD

This application claims priority to U.S. Provisional Application No. 62/009,777 filed Jun. 9, 2014, the entire content of which is hereby incorporated by reference.

This invention was made with U.S. Government support under grant IIS-1162095, awarded by the National Science Foundation; and grant EB015638, awarded by the Department of Health and Human Services, the National Institutes of Health (NIH). The U.S. Government has certain rights in the invention.

BACKGROUND

1. Technical Field

The field of the currently claimed embodiments of this invention relates to tracking systems and methods, and more particularly to a virtual rigid body optical tracking system and method.

2. Discussion of Related Art

Image-guided surgery systems are frequently used during surgery to provide surgeons with information support. For these systems to show their full capabilities and enable more advanced applications such as volume building or automated actuation, tools and devices must be registered together. An integral component to register these devices together is tracking. Conventional tracking is performed with electromagnetic (EM) or optical trackers. A sensor or marker is placed on the device, and the tracker reports the pose of the sensor or marker. In general, conventional tracking technologies are fairly accurate and can achieve sub-millimeter tracking errors. However, both EM and optical trackers have limitations. EM sensors do not require line of sight, but their accuracy is compromised in the presence of metal tools. This is a fairly significant limitation as many tools and devices must be avoided if one intends to use an EM tracker.

Optical trackers, on the other hand, do not suffer from metallic distortion. The first limitation for optical trackers are that they do require a line of sight between the optical tracker and the optical marker. The second limitation is that the size of the optical marker is limited by the size of the tool and the crowded surgical workspace. There has been some research in the design of optical markers [1]. However, there remains a need for improved optical tracking systems and methods.

SUMMARY

According to some embodiments of the present invention, a virtual rigid body optical tracking system includes a virtual rigid body generator for projecting a virtual rigid body, wherein the virtual rigid body forms a pattern of light on a surface. The virtual rigid body optical tracking system includes an optical detection system for detecting the pattern of light, and a data processing system in communication with the optical detection system. The data processing system is configured to determine a position of the virtual rigid body generator based on the detected pattern of light.

According to some embodiments of the present invention, a method for virtual rigid body optical tracking includes projecting a virtual rigid body, wherein the virtual rigid body forms a pattern of light on a surface, detecting the pattern of light, and determining a position of a generator of the virtual rigid body based on the detected pattern of light.

According to some embodiments of the present invention, an inverse virtual rigid body optical tracking system includes first and second scanning light sources for scanning an area in which an operator utilizes a tool to be tracked, and a photodiode attached to the tool to be tracked. The photodiode is configured to receive light from the first scanning light source and the second scanning light source. The inverse virtual rigid body optical tracking system also includes a data processing system in communication with the first scanning light source, the second scanning light source, and the photodiode. The data processing system is configured to determine an orientation of the first scanning light source when the photodiode received light from the first scanning light source, and an orientation of the second scanning light source when the photodiode received light from the second scanning light source. The data processing system is further configured to determine a position of the tool based on the orientation of the first scanning light source and the second scanning light source.

BRIEF DESCRIPTION OF THE DRAWINGS

Further objectives and advantages will become apparent from a consideration of the description, drawings, and examples.

FIG. 3A illustrates a clinical scenario in which an ultrasound guided needle biopsy using a virtual rigid body;

FIG. 3B illustrates a minimally invasive tracked ablation using a virtual rigid body;

FIG. 4A shows the notation and parameterization of a projection pyramid consisting of three lines according to some embodiments of the invention;

FIG. 4B shows the notation and parameterization of a projection pyramid consisting of four lines according to some embodiments of the invention;

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
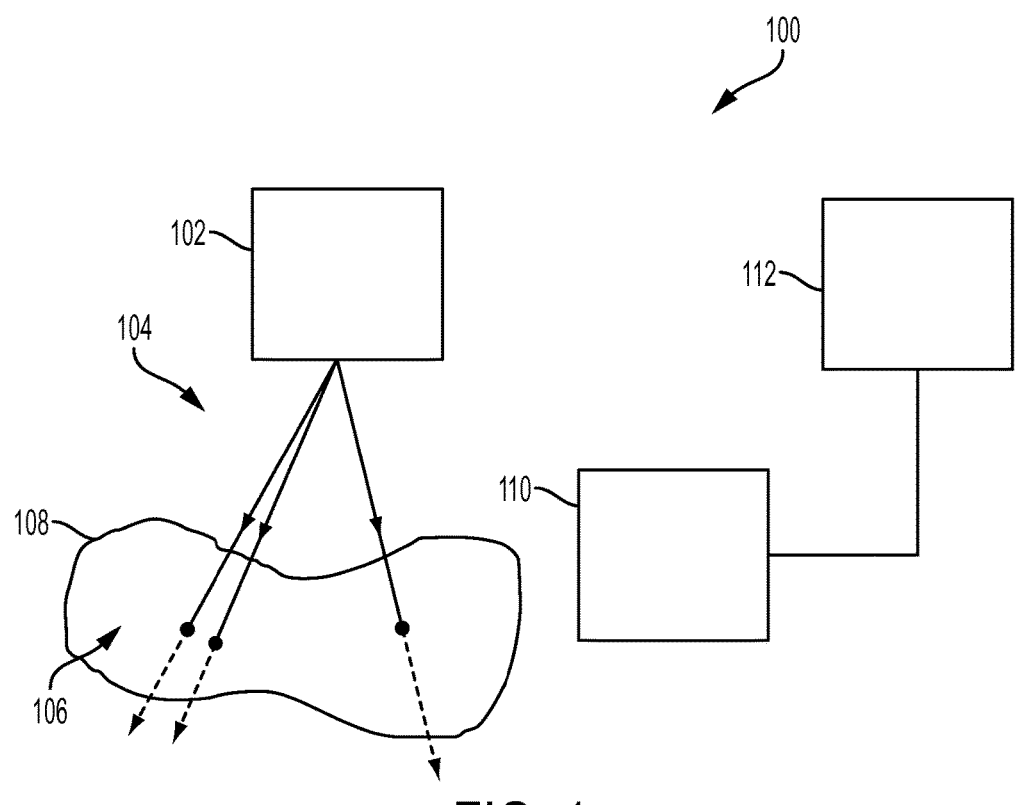
FIG. 1 is a schematic illustration of a virtual rigid body optical tracking system according to some embodiments of the current invention.

A virtual rigid body optical tracking system according to some embodiments of the invention is shown in FIG. 1. The virtual rigid body optical tracking system 100 includes a virtual rigid body generator 102 for projecting a virtual rigid body 104, wherein the virtual rigid body 104 forms a pattern of light 106 on a surface 108. The virtual rigid body optical tracking system 100 includes an optical detection system 110 for detecting the pattern of light 106, and a data processing system 112 in communication with the optical detection system 110. The data processing system 112 is configured to determine a position of the virtual rigid body generator 102 based on the detected pattern of light.

According to some embodiments of the invention, the data processing system 112 is further configured to reconstruct the virtual rigid body 104 based on the detected pattern of light, wherein the determination of the position of the virtual rigid body generator 110 is based on the reconstructed virtual rigid body. According to some embodiments of the invention, the virtual rigid body generator 102 comprises a plurality of laser diodes. According to some embodiments of the invention, the virtual rigid body generator 102 comprises a projector.

The terms "optical" and "light" are intended to have a broad meaning to refer to both visible and non-visible regions of the electromagnetic spectrum. For example, ultraviolet, near infrared and infrared light are intended to be included within the broad scope of the current invention.

Figure 2:
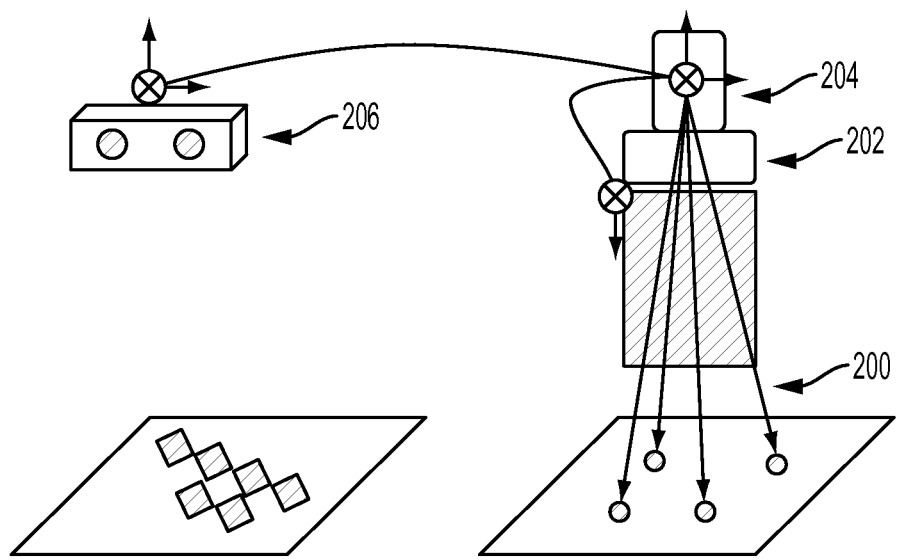
FIG. 2 illustrates the concept of using a virtual rigid body for tracking an ultrasound transducer.

Some embodiments of the current invention address the limitations of optical trackers by providing an optical tracking paradigm using a virtual rigid body (VRB). The VRB is a 3D marker generated from a light projection device, resulting in a light pattern being projected onto some surface. By detecting this pattern, one can reconstruct the 3D marker and track the VRB. FIG. 2 illustrates the use of a virtual rigid body 200 to track an ultrasound transducer 202. A virtual rigid body projector 204 is attached to the ultrasound transducer 202, and projects the virtual rigid body 200. An optical detection system 206 detects the pattern (for example, dots or a checkerboard) projected on a region of interest, and a data processing system can use the detected pattern to determine the location and orientation of the ultrasound transducer 202.

FIG. 3A illustrates a clinical scenario in which an ultrasound guided needle biopsy using a virtual rigid body. FIG. 3B illustrates a minimally invasive tracked ablation using a virtual rigid body Like conventional markers, the VRB generator can be attached to the tool. While a line of sight is still required between the optical detection system and the light pattern projected onto the surface, there can be built-in redundancy in the VRB so that occluded parts of the pattern will not prevent successful tracking. This is a relaxation of the typical optical tracking limitation as the line of sight is required to the surface of interest as opposed to the device attached to the tool. In a minimally invasive procedure where the camera or optical tracker is providing the primary surgical view, this is not a difficult requirement to satisfy. This type of occlusion is unlikely to occur as the camera must always maintain its view of the region of interest. The other type of occlusion that could occur is between the virtual rigid body generator and the surface. However, since light is being projected, some or all of the points will simply be on the surface occluding the original surface, allowing this method to work with any arbitrary surface.

The virtual rigid body generator that is being tracked may be attached to another medical tool or device, allowing the tool or device to be tracked after a standard calibration process. Two examples of the calibration process are ultrasound (US) calibration[2] for tracked US images or pivot calibration for tracked needle tips. In conventional optical tracking, the marker attached to the tool must always be within the optical tracker's field of view (FoV). With the VRB, the tool or virtual rigid body generator can be outside of the optical detection system's FoV as the pattern will still be projected onto the surface. This is illustrated in FIG. 3A, which shows that the optical marker is far away from the patient surface, whereas the projected VRB is directly on the patient surface. Also, optical trackers generally have regions with varying RMS errors, so it is beneficial to minimize the size of the tracking region. The VRB allows the optical trackers to focus on a single region of interest as opposed to each tracked tool in addition to the region of interest.

A VRB optical tracking system according to some embodiments of the invention can have the following features. The virtual rigid body generator can be self-contained. There is no need to wire it as in optical tracking or electromagnetic tracking. For example, a miniaturized solar cell can be integrated to the light source. This cell can be charged from the intraoperative field or from the projector available with the camera system. This virtual rigid body generator can be totally passive and the main line of lights can be generated through light reflection from a main projector. The virtual rigid body generator can be made of a single LED included in, for example, a small top of a pyramid with holes at the edges and at the top center of the pyramid. It is important to note that the shape can be any unique 3D shape. Alternatively, a diffraction pattern can be added to produce specific number of light points. Also, the light source can be a pulsed light source in a visible mode to both used for VRB and to create a photoacoustic effect as described in the following sections.

With this approach, there is no need for a sophisticated and offline calibration procedure to recover the relative location of the tool with respect to the virtual rigid body. For example, the current stereo camera system can identify the 3D location of the needle and at the same time identify the light points emanating from the rigid body, and hence get the offset uniquely identified from a single pose. Additionally, the tip of the virtual rigid-body (i.e. the top point of the pyramid) does not need to be identified if there are enough points located on the surface and if the geometry of the virtual rigid-body is known. Registration methods similar to iterative closest point (ICP) are known to a trained person in the art to recover the pose.

According to some embodiments of the invention, the virtual rigid body is one in which the tracked marker is a light source and an optical detection system is used to detect the light. The optical detection system may include a stereocamera system. The stereocamera system may be any system that is capable of acquiring camera images of the observed scene and determining the three-dimensional position of any observed point in the images with triangulation [13]. This could be a multi-camera setup with a known transformation between the cameras. This could also be a single tracked camera so that a transformation between the images can be determined from the tracking information. Different setups can provide varying levels of fields of view and robustness. The stereocamera system may be multiple cameras registered together, or single camera with a structured light projector. The stereocamera system may be a combination of the systems described above. The optical detection system enables tracking with the virtual rigid body, and is an integral component of the system.

The virtual rigid body generator may include laser diodes, or any setup capable of projecting collimated beams of light. This could be laser diodes, miniature laser pointers, focused light emitting diodes, or a laser projector. The laser diodes can project collimated beams of light in a known configuration. These beams of light hit a surface and these points can be seen by a stereocamera. A data processor can recover the pose and orientation of the virtual rigid body generator attached to any tool from the detected pattern of light.

The virtual rigid body generator may be capable of projecting multiple focused beams or an arbitrary pattern of light onto a target surface. A possible implementation to generate focused beams of light would be a plurality of laser pointers or laser diodes arranged in a known configuration. A possible implementation to enable both focused beams and an arbitrary pattern of light would be a projector.

The virtual rigid body generator may comprise three or more laser diodes with wavelength modulation. The three or more laser diodes can be used to project light at different wavelengths. According to some embodiments of the invention, each of the laser diodes projects light at a unique wavelength. The data processor can then establish a correspondence between the projected collimated beams of light and the points observed by the optical detection system on a surface, since the points will appear as different colors. Since the projection geometry is known, the data processor can register the observed points to the shape defined by the projection geometry, i.e., using the pair-wise distances between points. This is feasible with just four points if there is an established correspondence. This results in the projection system's pose and orientation being defined within the optical detection system's coordinate system.

According to some embodiments of the invention, the virtual rigid body generator may comprise three or more laser diodes with time modulation. According to some embodiments, each laser diodes can project light with unique a time modulation. The data processor can then established a correspondence between the projected collimated beams of light and the points observed by the optical detection system on a surface, since the points will have different time modulations. An implementation of this concept according to some embodiments of the invention is direct synchronization between the VRB light source and the detecting camera. Such synchronization can lead to sub-pixel detection of these points by relying on known image processing methods. The term "point" is not meant to be limiting, and can include, for example, a line, a cross, a circle, and other shapes and markings.

According to some embodiments of the invention, the virtual rigid body generator may comprise n laser diodes without correspondence. For example, n laser diodes projecting the same color may be used. A correspondence can be established between the projected collimated beams of light and the points observed as in the cases for three or more lasers, except that there will be n points for a registration without established correspondence.

According to some embodiments of the invention, an ultrasound imaging system comprising a virtual rigid body generator may include an ultrasound transducer that enables real-time interoperative imaging. The ultrasound transducer may be tracked by the virtual rigid body generator, the virtual rigid body, and the stereocamera system, so that the images obtained from the ultrasound transducer can be used to update any pre-operative plans.

The virtual rigid body is a projected light pattern that can be used to track the virtual rigid body generator. The light pattern is projected onto a surface and is observed by the optical detection system. A data processor can then uniquely fit the observed pattern to the light projection model, allowing the pose of the virtual rigid body generator to be determined. The projected light pattern can also be dynamically modified. For example, it may be beneficial to project the light pattern onto a specific region of the images observed by the optical detection system. Dynamic light patterns also enable the segmentation of the pattern with motion.

A general-purpose virtual rigid body generator is a 6 degree-of-freedom tracking device. A pattern is projected from the VRB generator onto an arbitrary surface. Images of this pattern allow for recovery of the 6 degree-of-freedom pose.

The following examples describe some further concepts of the invention with reference to particular examples. The general concepts of the current invention are not limited to the particular examples.

EXAMPLES

As can be seen in FIG. 2, the VRB is a 3D marker generated from a light projection device, resulting in a light pattern being projected onto a surface. It is generally known that a larger marker will result in higher accuracy, but the size of the marker can be limited by the crowded surgical workspace. However, the size of the VRB is no longer limited by its physical size, but rather the field of view of the optical tracker. This is an advantage of using the VRB, as it is feasible to create a large marker in a limited surgical workspace. FIGS. 3A and 3B show that the projected VRB is much larger than the optical marker. This type of optical tracking could allow for a smaller form factor than conventional tracking methods. Also, the VRB can be customized to project any pattern. For example, if the tracked tool is likely to be far away from the region of interest, then it may be preferable to have a VRB with a more compact pattern such that most of the pattern is within the optical tracker's FoV.

To convey the use of the VRB with a more concrete example, we will describe the clinical scenario shown in FIG. 3B. During a minimally invasive guided liver ablation, the surgeon will generally have access to a stereo-endoscopic camera and an ablation device. The device that generates the VRB will be rigidly attached to the ablation tool, projecting some pattern onto the liver surface. It is assumed that the rigid body transformation between the VRB's coordinate frame and the ablation tool tip is found pre-operatively with a calibration process. The stereo-endoscopic images are processed to track the VRB and consequently the ablation tool. These stereo-endoscopic images could also be used to digitize the liver surface and register it to some pre-operative ablation plan. Visual cues can then be displayed to the surgeon to help them position and orient the ablation tool when executing their pre-operative plan.

There has been work in the virtual reality field on the design of six degree of freedom tracking devices. Systems such as Kinectrack [5] and Sceptre [6] track projected patterns of light on planar surfaces to deduce the six degree of freedom pose of the emitter. These works assume that the surfaces are either planar or piecewise-planar. This is a valid assumption in virtual reality environments as there are either a large number of projected points or the surface is a planar screen. However, in image-guided interventions, there are rarely planar surfaces in the human body. As such, a method is needed for tracking the projection device based on a set of projected points on an arbitrary surface. To the best of our knowledge, this is the first application of projected light as a tool tracking method in medical applications.

The VRB concept stems from using some projection device to project a light pattern onto some surface. Given an observation of this pattern using an external tracker, such as a stereocamera (SC) system, the pose of the projection device can be determined. This concept is demonstrated using a triangular base pyramid as the VRB, though many other projection configurations can be used. As can be seen in FIGS. 4A and 4B, the VRB according to some embodiments of the invention consists of three (FIG. 4A) or more lines (FIG. 4B) representing the projection device's respective beams of light, each fully described by its unit vector, $u_i$. The number of lines shown in FIGS. 4A and 4B is simply an example, and more projection vectors are also feasible. The apex of the projection pyramid is set as the origin of the projection pyramid coordinate system. The lines can be parametrized such that any point on the line is defined by a scale factor, s. The point where the beams of light intersect the surface can therefore be described as $s_i u_i$ in the projection pyramid coordinate system. Thus, given an observation of the surface and beam intersection points, p, in the SC's coordinate system, the pose of the projection pyramid's apex described in the SC's coordinate system can be recovered. Liu et al [7] previously used a similar approach to recover the pose of a plane intersecting such a pyramid.

$$\forall i,j \text{ and } i \neq j \; d_{ij}^2 = \|p_i - p_j\|^2 \tag{1}$$

$$\forall i,j \text{ and } i \neq j \; d_{ij}^2 = \|s_i u_i - s_j u_j\|^2 \tag{2}$$

$$\forall i,j \text{ and } i \neq j \; d_{ij}^2 = s_i^2 - s_j^2 2 s_i s_j \cos \theta_{ij} \tag{3}$$

To show that this approach is feasible, a set of $d_{ij}$ is first defined using equation (1), which represents the distances between the 3D surface and beam intersection points, p, seen by the SC. The non-linear optimization problem described in equation 2 is then solved, and the set of s is found. Assuming that the set of projection unit vectors, u, is unique, it is clear that a solution s can be obtained from equation (2). This is a valid assumption as one can have full control over the choice of each $u_i$. However, there is still an uncertainty whether the solution s is unique given a set of $d_{ij}$.

$$d_{12}^2 = s_1^2 + s_2^2 \tag{4}$$
$$d_{23}^2 = s_2^2 + s_3^2$$
$$d_{13}^2 = s_1^2 + s_3^2$$

$$s_1 = \pm \sqrt{\frac{d_{12}^2 - d_{23}^2 + d_{13}^2}{2}} \tag{5}$$

$$s_2 = \pm \sqrt{\frac{d_{12}^2 + d_{23}^2 - d_{13}^2}{2}}$$

$$s_3 = \pm \sqrt{\frac{-d_{12}^2 + d_{23}^2 + d_{13}^2}{2}}$$

Equation (2) can be rewritten as equation (3) where represents the angle between $u_i$ and $u_j$. It will be shown that the solution s is unique when there are three orthogonal projection vectors, u. If they are orthogonal, then $\cos \theta_{ij} = 0$ and equation (3) can be rewritten as the set of equations in (4). These three equations are independent of each other and can be manipulated to isolate for each individual $s_i$ as shown in the set of equations in (5). Since there is a positive and negative solution for each $s_i$, there are a total of eight possible solutions. However, all negative $s_i$ are invalid as the projection is only in the positive direction. There is only a single solution of s wherein each $s_i$ is positive. Thus, it has been shown that the solution s is unique when the three projection vectors, $u_i$, are orthogonal.

Any assumptions of the projection vectors can be enforced since they are chosen by the user. However, there are some cases where orthogonal projection vectors are limiting. For example, if the projection device is far away from the surface, then the projected points on the surface will also be far apart and possibly outside of the optical tracker's or SC's FoV. Thus, it can be beneficial to relax the assumption that the projection vectors are orthogonal. Here, the effects that non-orthogonal projection vectors will have on the uniqueness of the solution are presented herein. For example, if one of the projection vectors is taken to be orthogonal to the other two, such that $\cos \theta_{13} = 0$ and $\cos \theta_{23} = 0$, the solution can be obtained from the equations shown in equation (6) below. It can be shown that there are four possible solutions for $s_3$, of which two will always be negative. From this, it can be seen that there are 8 possible solutions in this case, but if the negative solutions are removed from $s_1$ and $s_2$, there are only two viable solutions as $s_1$ and $s_2$ are completely defined by the choice of $s_3$.

$$s_1 = \pm \sqrt{-s_3^2 + d_{13}^2}$$

$$s_2 = \pm \sqrt{-s_3^2 + d_{23}^2}$$

$$2 s_3^2 + \frac{2 c p s \, \theta_{12}}{\sqrt{s_3^4 - s_3^2 d_{23}^2 - s_2^2 d_{13}^2 + d_{13}^2 d_{23}^2}} + d_{12}^2 - d_{13}^2 - d_{23}^2 = 0 \tag{6}$$

A similar situation occurs when only one pair of projection vectors are taken to be orthogonal. For example, if only $\cos \theta_{23} = 0$, it can be shown that there will be two positive solutions for $s_1$. For each of these two solutions, either $s_2$ or $s_3$ can have two viable solutions, but $s_2$ is completely defined by $s_3$ and vice versa. Thus, there are four viable solutions in this case. When none of the projection vectors are orthogonal, there are eight possible solutions. Four of these solutions will be associated with the negative projection, leaving four viable solutions. Thus, for all cases where some or all of the projection vectors are non-orthogonal, an additional projection vector is needed to uniquely identify the solution. This added projection vector provides additional constraints as there are now six equations of the form (3) solving for four unknowns, $s_1 \ldots s_4$, as opposed to three equations of the form (3) solving for three unknowns. Alternatively, one can rely on more than one reading of the VRB. Typically, as the tool is moved in the surgical field, one can easily apply regularization by assuming smooth changes of the six degrees-of-freedom and hence other viable solutions can be filtered out.

The apparatus used to generate a virtual rigid body according to some embodiments of the invention is now described. According to some embodiments, laser pointers are physically arranged such that the beams of light form a projection pyramid. The laser pointers are fixed by two acrylic plates and are well below the safety limits for applying laser energy onto human tissue. The laser pointers are also chosen to emit different wavelengths of light. According to some embodiments, the laser pointers projected red, blue, and green light respectively. This allows the correspondence between the points seen in the SC and the projection vectors of the projection pyramid to be recovered.

Figures 5A, 5B:
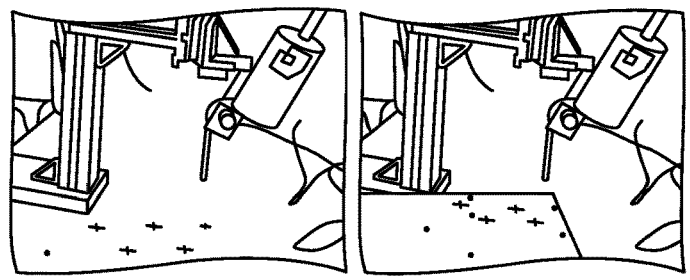
FIG. 5A shows a pattern projected on a lower surface.
FIG. 5B shows the pattern of FIG. 5A projected on a higher surface.
Figure 6:
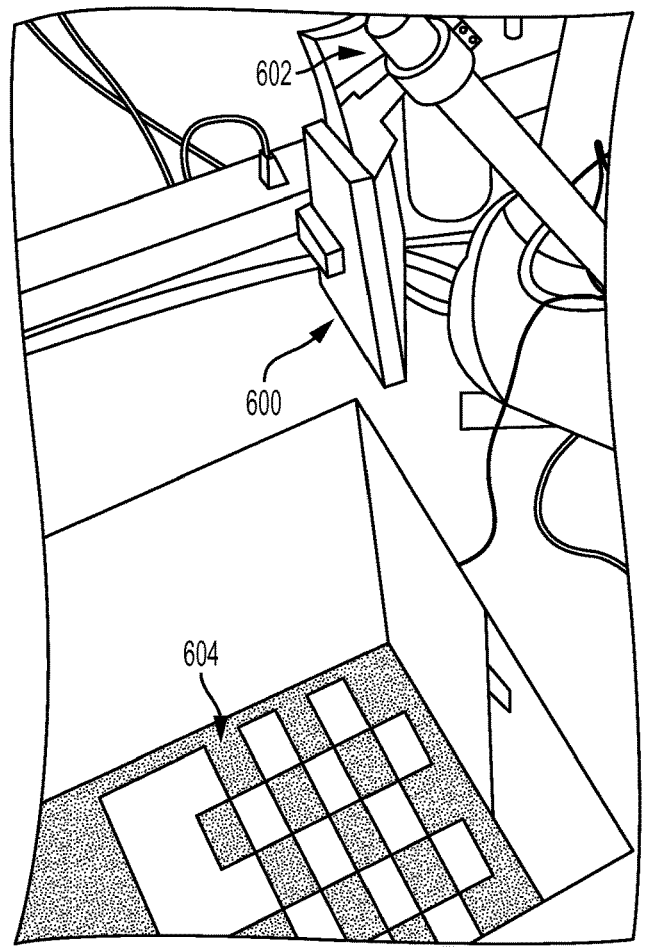
FIG. 6 shows a virtual rigid body experimental setup including a robot arm, a virtual rigid body projector, and a projected pattern.

According to some embodiments of the invention, a Microvision Showwx projector (Microvision, Inc., Washington) is used in place of laser pointers. Since a projector simply projects an image, the user now has complete control of what is projected. Different projection pyramids and spot patterns are easily configurable. Additionally, custom acrylic plates do not need to be manufactured to position laser pointers in various positions, as laser pointers are not required. A projector can be used out of the box as an optical tracker using the methods described herein. The projector used according to some embodiments of the invention is shown in FIGS. 5A, 5B, and 6.

In addition to the projection device, the optical tracking system with a virtual rigid body according to some embodiments of the invention also includes an SC system. A custom-built SC system containing two CMLN-13S2C cameras (Point Grey Research, Richmond, British Columbia, Canada) can detect the projected points and allows them to be triangulated into points in the SC coordinate system. A typical SC marker is also attached to the projector so that a comparison between conventional optical tracking and virtual rigid body optical tracking can be made. According to some embodiments, a MicronTracker Sx60 (Claron Technology, Toronto, Ontario, Canada) is used as the SC system. In this setup, the optimized marker detection algorithms present within the MicronTracker software development kit can be leveraged. The field of view of these cameras is approximately 40°, though the concepts of the invention are not limited to cameras with this field of view. Cameras with larger and smaller fields of view may also be used.

According to some embodiments of the invention, an actuator can be attached to the projection device to move it in an automated or cooperative manner. According to some embodiments, a UR5 robotic arm (Universal Robots) is used as the actuator. FIG. 6 shows a virtual rigid body projection device 600 attached to a robot arm 602. The rigid body projection device 600 projects a pattern 604.

According to some embodiments of the invention, the projector is used to project a scene consisting of points and crosses. There are a couple of things to note in this projected image. First, there are two sets of virtual markers: the points in the corner, and the crosses within the projected image. Both of these sets of virtual markers can be used interchangeably. The main difference is in how these points are segmented as it was qualitatively easier to pick the center point of the crosses as opposed to the corner points. Second, the position of these corners and crosses in the projected image, the projector's display resolution, and its throw ratio define the projection vectors. It is also possible to recover the projection vectors from a calibration process. Two sets of images of the points projected onto two different surfaces, acquired without moving the SC or the projection device, are necessary for this process. An example pair of these images is shown in FIGS. 5A and 5B. By segmenting and triangulating each of these three-dimensional points in the images and subtracting the points in one image from the points in the other image, the resulting vectors will be a scaled version of the projection vectors. An alternative shown in FIG. 6 is a projection of a checkerboard, which can be interpreted as a grid of points or crosses. This alternative allows for more robust automatic segmentation, but the increased projection area may occlude the scene.

There are three algorithmic components that enable optical tracking with the virtual rigid body: 1) Segmentation of the points in the SC images, 2) Finding the segmented points in the projection pyramid's coordinate system, and 3) Finding the rigid body transformation between the projection pyramid and the SC. The segmentation is currently done manually as that is not a focus of this work and it was felt that manual segmentation was more accurate. The second component can be acquired by solving equation (7) for $s_i$ using non-linear optimization based on trust region reflective [8] or Levenberg-Marquardt [9, 10] methods. It is also possible to solve the system of equations in (3). In the case of three orthogonal projection vectors, solving the system of equations can be advantageous as there is no guarantee that the optimization will return the desired solution of the eight solutions that satisfy the system. However, in the case of four non-orthogonal projection vectors, optimization can be advantageous as the system of equations becomes overdefined and any noisy measurements will result in no solution.

$$\min F_{ij} s.t. \forall i=1 \ldots n, j=1 \ldots m, i \neq j : F_{ij} = abs(\|s_i u_i - s_j u_j\| - d_{ij}) \quad (7)$$

After the second step, one will have a set of points in the SC coordinate system, $p_i$, and a set of corresponding points in the projection pyramid coordinate system, $s_i u_i$. With these two sets of points, the third component involves solving for the rigid body transformation between these two sets of points using Arun's method [11] or Horn's method [12]. This is shown in equation (8), where $T_p^{SC}$ is solved for, which brings points in the projection pyramid space into the SC space. This rigid body transformation is found, the projection pyramid coordinate system can be transformed into the SC coordinate system, resulting in the complete pose of the projection pyramid's apex in the SC coordinate system. The apex of the projection pyramid in the SC coordinate system, $a_i$, can be found using equation 9.

$$p_i = T_p^{SC} s_i u_i \quad (8)$$

$$a_i = T_p^{SC} [0\ 0\ 0\ 1]^T \quad (9)$$

The virtual rigid body comprising a plurality of laser pointers was tested by holding it with a passive arm and re-projecting the projection pyramid in the SC space. This was done because there was not an effective way to move the virtual rigid body apparatus with known distances.

To test the virtual rigid body comprising a projector, the projector is held by a passive arm in a set of poses with known distances, $k_{ij}$, between them. The set of distances are approximately 2.5 mm. For each of these poses, a set of SC images are taken. Each of these SC pairs result in the pose of the projection pyramid's apex in the SC coordinate system, the position of which is the apex, $a_i$, and the position of the SC marker, $m_i$. A distance metric is computed for the pairs of $(a_i, a_j)$ and $(m_i, m_j)$ in equations (10) and (11). A targeting error can then be computed using the distances obtained from the virtual rigid body as in equation (12) and using the distances obtained from the conventional optical marker as in equation (13). The test of the second generation virtual rigid body was repeated using the experimental setup with the custom SC system and the MicronTracker.

$$d_{aij} = \|a_i - a_j\| \quad (10)$$

$$d_{mij} = \|m_i - m_j\| \quad (11)$$

$$\forall i=1 \ldots n-1, j=i+1 : D_{ij} = |d_{aij} - k_{ij}| \quad (12)$$

$$\forall i=1 \ldots n-1, j=i+1 : M_{ij} = |d_{mij} - kij| \quad (13)$$

Another test was performed using a UR5 robotic arm (Universal Robots) in place of the passive arm. This allows us to have known motions which include rotations between multiple poses. The metric used for the second experiment is derived from the magnitude of the motion. Each motion can be represented as a transformation matrix, $F=[R,t]$. We can compare d when the motion is translation only and $\theta$ when the motion is rotation only, where these two values are computed from equation (14) and (15) respectively. In equation (15), $e^{\theta N}$ denotes the matrix exponential and N is the skew symmetric matrix generated from the vector representing the axis of rotation.

$$d = \text{norm}(t) \quad (14)$$

$$R = e^{\theta N} \quad (15)$$

Figure 7:
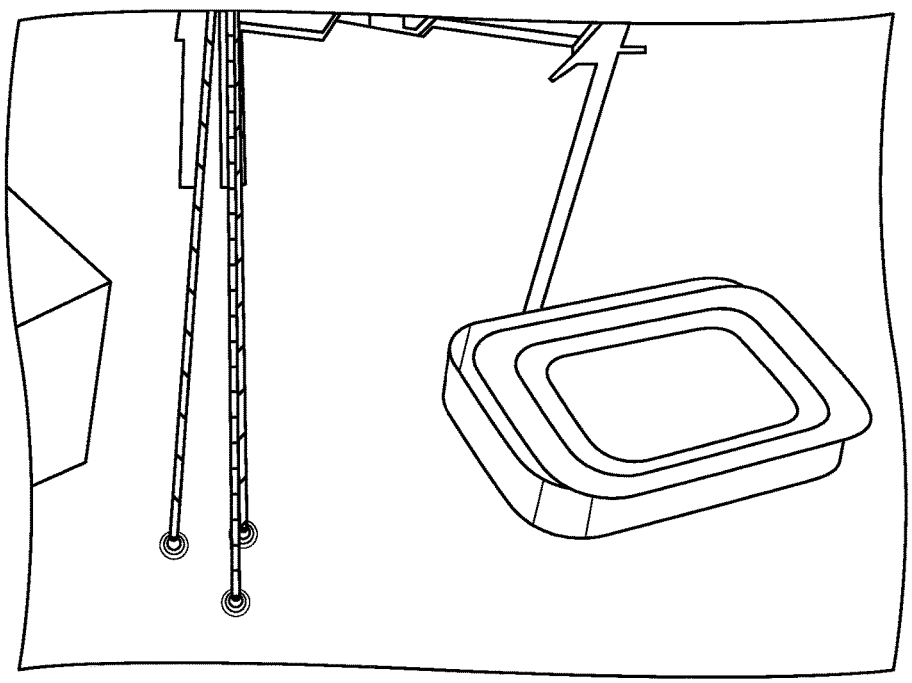
FIG. 7 shows a projection pyramid reprojected in the stereocamera (SC) space.

The qualitative results from testing the first generation of the virtual rigid body can be seen in FIG. 7, which shows the projection pyramid reprojected in the SC space.

The results for the experimental setup with the custom SC system were computed over thirty-six poses obtained from the crosses and the marker. The mean and standard deviation of $D_{ij}$ was 0.40 mm±0.29 mm and the mean and standard deviation of $M_{ij}$ was 0.69 mm±0.42 mm.

The results for the experimental setup with the Micron-Tracker were computed over 16 poses in a 3.8 mm spaced 4-by-4 grid. For this set of results, we compared all of the distances between each pair of poses. The mean and standard deviation of $D_{ij}$ was 0.38 mm±0.28 mm and the mean and standard deviation of $M_{ij}$ was 0.23 mm±0.22 mm.

The results for the experiment with the robotic arm was computed over 24 poses. The mean and standard deviation for the difference in d was 0.18±0.10 mm for the virtual rigid body and 0.03±0.02 mm for conventional optical tracking. The mean and standard deviation for the difference in $\theta$ was 0.50±0.31 degrees for the virtual rigid body and 2.68±2.20 degrees for conventional optical tracking.

There are several observations to be made from the results. First of all, the errors of the optical tracking method are comparable to those of conventional optical tracking. It can be seen that, in the first set of experiments with the custom SC system, the errors using the virtual rigid body were lower than conventional optical tracking. In contrast, for the second set of experiments with the MicronTracker, the errors using the virtual rigid body were higher than conventional optical tracking. One important distinction to note between the virtual rigid body and the conventional optical marker is that the virtual rigid body can be used to recover the position and orientation, whereas the marker can only recover the position. Another likely reason is that the MicronTracker is optimized to segment the attached markers. As seen in the third set of results, the rotational errors are much better when using the VRB than when using the conventional optical marker. One possible reason for this is that the VRB has better rotational sensitivity. Any rotation experienced at the tool will have its effects magnified on the projected pattern. More experiments must be conducted to evaluate when the size of the virtual fiducial overcomes its inherent disadvantage in segmentation. One result that seems slightly odd is that the translational error using a conventional marker is even lower than the rated robot arm precision. Since the collected motions were about the robot's principal axes, the change in gravity and the associated gravity compensation mechanisms are minimal. Thus, the robot arm's precision may have been better than the rated value in the motions that we selected to use.

According to some embodiments of the invention, the projection system is miniaturized. The projector used according to some embodiments may be inadequate for a real application as it requires wired power and a processor. However, it serves as an ideal prototype as it allows for flexibility in the projection pattern. Miniaturization of the project will also allow it to be attached to the tool or device that is to be tracked. According to some embodiments of the invention, a fiber delivery or laser diode system are employed. According to some embodiments of the invention, a light emitting diode with a mask is used to generate a pattern. According to some embodiments of the invention, a light source that emits infrared light is used. This combined with a SC system that receives infrared light can greatly aid in automatic segmentation. According to some embodiments, the SC system can be a system that only receives infrared light.

While it is expected that automatic segmentation may degrade the results, there are some developments that can make automatic segmentation more reliable. For example, the projected pattern is not limited to points. A checkerboard grid can be used instead as an intersection of edges is generally easier to automatically detect than points. There are some methods [4] in the structured light field that can be used to robustly detect these grids and also establish correspondence. This type of pattern would also allow the 3D representation of the surface to be recovered, which could be one possible method to reference the patient.

Lighting is an important consideration if one wishes to use the intensity and wavelength of the projected light for segmentation and correspondence. One can either use wavelengths that do not interfere with the surgical lighting or use structured light approaches that depend less on wavelength. One related challenge in establishing correspondence is when multiple tracked tools are present. One could use coding strategies wherein the patterns are independently or selectively turned on or off. Wavelengths that are distinguishable from each other can also be used.

Figure 8:
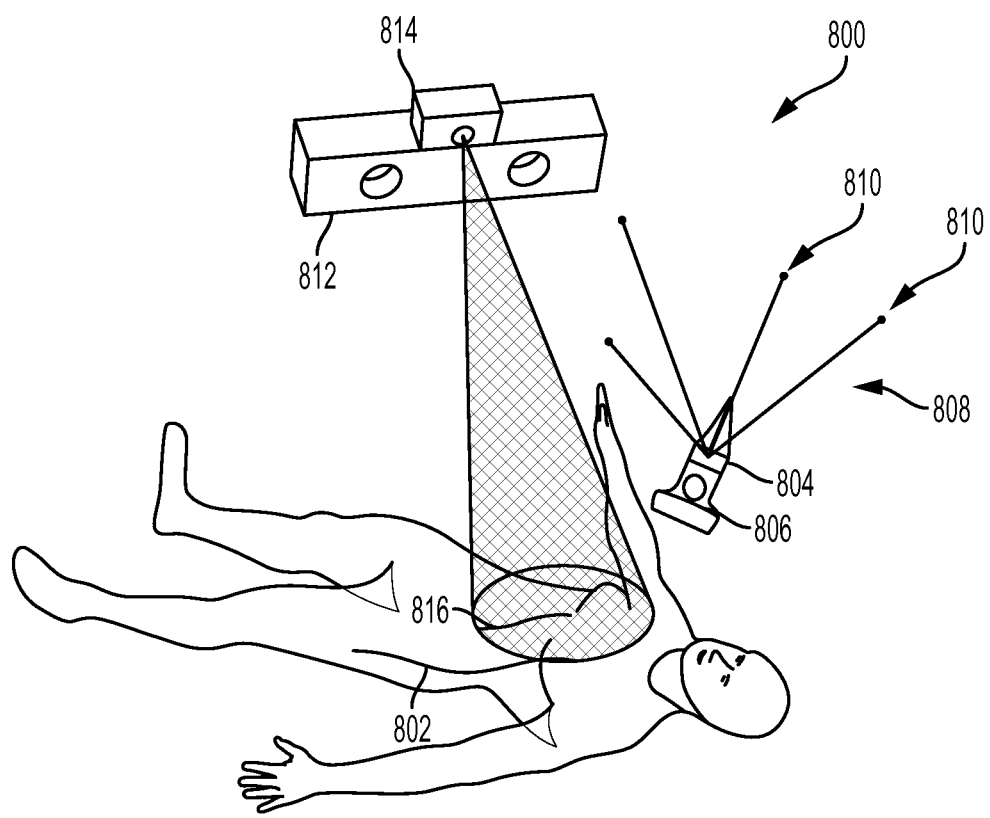
FIG. 8 shows a virtual rigid body optical tracking system for tracking a catheter.

Methods for tracking a catheter using a VRB according to some embodiments of the invention are now described. The VRB can be used as an ultrasound transducer tracker and as a photoacoustic tracker. FIG. 8 shows a virtual rigid body optical tracking system 800 for tracking a catheter 802. A virtual rigid body projector is attached to an ultrasound transducer 806. The virtual rigid body projector 806 projects a virtual rigid body 808 which forms a pattern 810 on a surface. In the example of FIG. 8, the virtual rigid body 808 is projected away from the patient's body, though the embodiments of the invention are not limited to this orientation. An optical detection system 812 can detect the pattern 810 and a data processing system can use the detected pattern to determine the position and orientation of ultrasound transducer 806. The data processing system can then use data from the ultrasound transducer 806 in combination with the determined position and orientation of the ultrasound transducer 806 to determine the position of the catheter 802. According to some embodiments of the invention, the VRB optical tracking system further includes a visualization projector 814 for projecting a visualization 816 onto the surface of the region of interest. The visualization 816 can be a projection of guidance information onto the surface.

Figure 9:
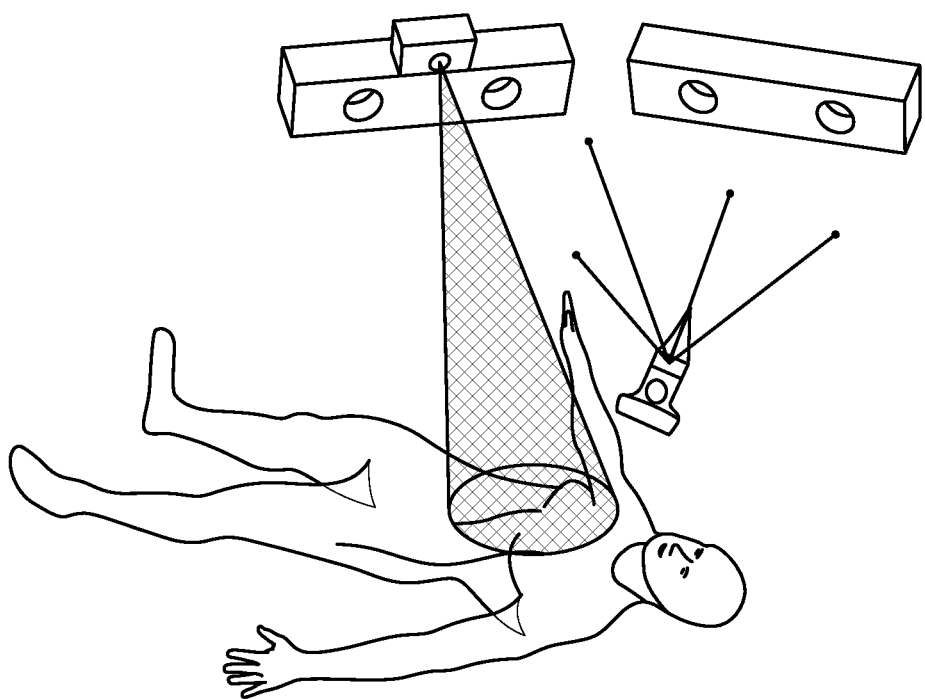
FIG. 9 shows a virtual rigid body optical tracking system for tracking a catheter, wherein the system includes multiple optical detection systems.
Figure 10:
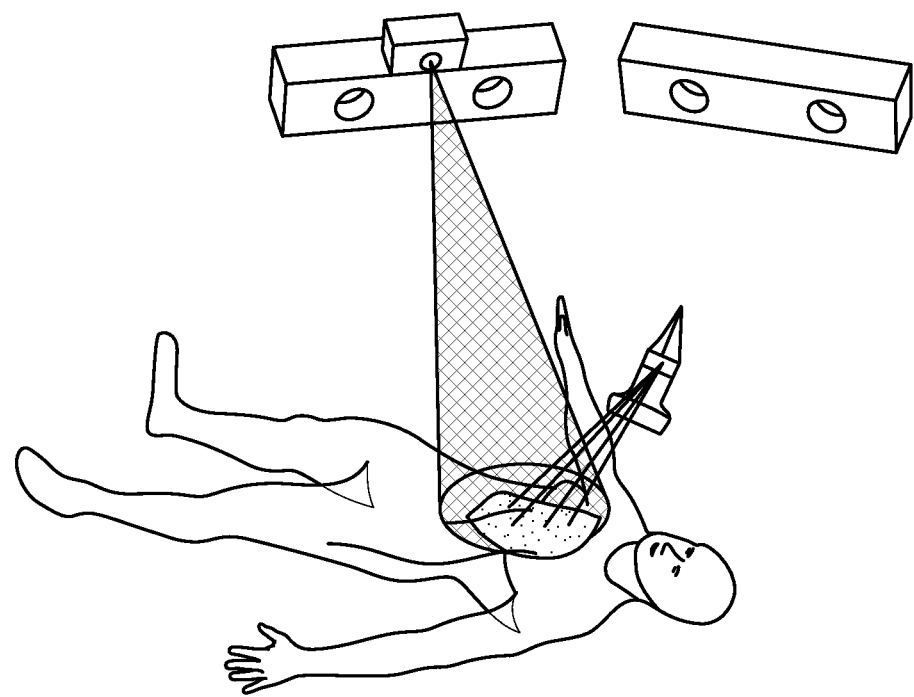
FIG. 10 shows a virtual rigid body optical tracking system for tracking a catheter, wherein the virtual rigid body is projected toward the patient's body.

FIG. 9 shows a virtual rigid body optical tracking system that is similar to the system shown in FIG. 8, but that includes multiple optical detection systems. The multiple optical detection systems can be calibrated with each other. FIG. 10 shows a virtual rigid body optical tracking system that is similar to the system shown in FIG. 9, but in this case the virtual rigid body is projected toward the patient's body.

Figure 11A:
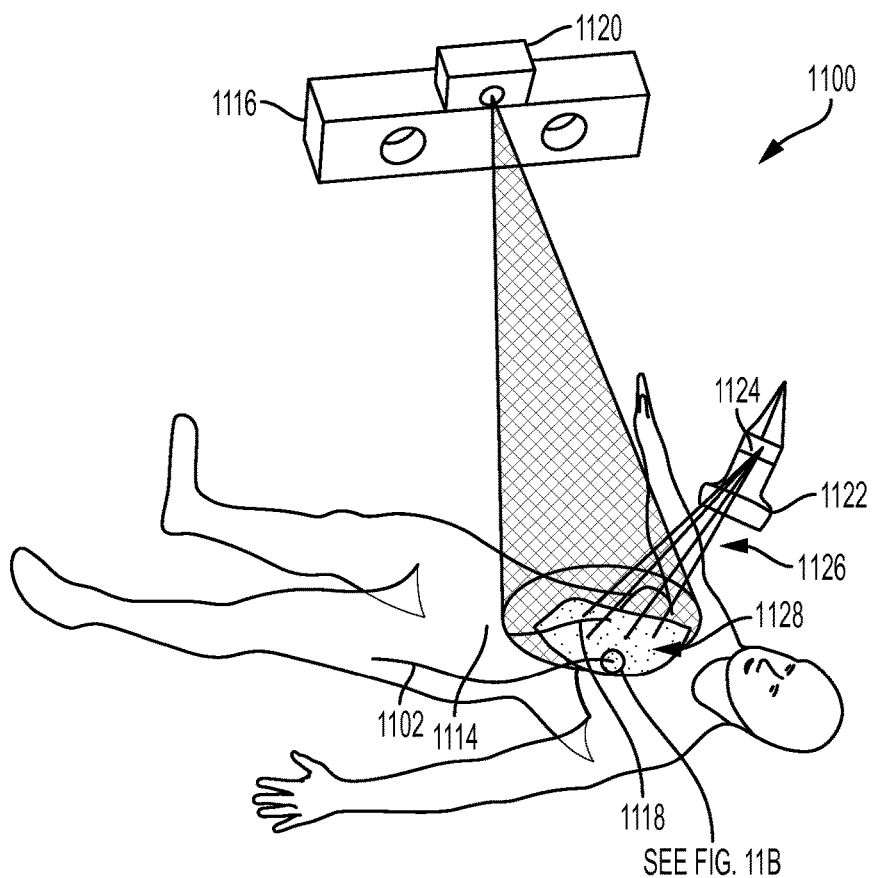
FIG. 11A shows a virtual rigid body optical tracking system for tracking a catheter according to some embodiments of the invention.
Figure 11B:
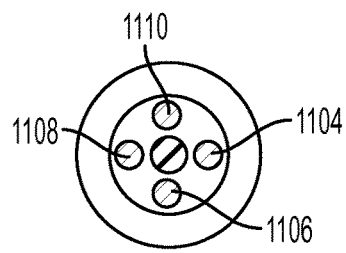
FIG. 11B shows a cross section of the catheter design of FIG. 11A.

FIG. 11A shows a virtual rigid body optical tracking system 1100 for tracking a catheter 1102 according to some embodiments of the invention. FIG. 11B shows a cross section of the catheter design. The catheter 1102 can include a hydrophone 1104. The hydrophone 1104 can be an optical fiber hydrophone or a piezoelectric hydrophone. The optical fiber hydrophone is an optical fiber with an interferometry structure on the tip or side. It converts the ultrasound pulse to an optical signal that is captured by an external equipment. The piezoelectric hydrophone is composed of a piezo-element and the electrical wire. In this case the ultrasound pulse is converted to an electrical signal through the piezoelectric effect. The hydrophone 1104 can receive the ultrasound signal transmitted from either an external ultrasound source, e.g. an external photoacoustic source, an imaging probe, or an ultrasound source included in the catheter. One or more hydrophones 1104 can be implemented in the catheter. With more than one hydrophone 1104 wherein the sensing elements are separate from each other, the catheter's pose can be monitored.

The catheter 1102 can include a photoacoustic (PA) fiber 1106. The PA fiber 1106 can be an optical fiber that connects an external pulsed laser source to the fiber tip. The PA fiber 1106 can deliver a pulsed laser to the catheter tip, and can illuminate the surrounding biological tissue to generate a PA signal. The PA signal can be captured by either external ultrasound sensors, e.g., ultrasound probes or hydrophones, or a hydrophone 1104 integrated into the catheter 1102. The PA signal can be used to image the surrounding tissue structure, localizing the catheter tip, sensing the biochemical constituents, or detecting the blood flow speed through the Doppler effect.

The catheter 1102 can include an ultrasound element 1108. The ultrasound element 1108 can be a piezoelectric element with electrical wiring or a PA element with an optical fiber. The ultrasound element 1108 can to transmit ultrasound pulses and/or receive ultrasound pulses. When the ultrasound element 1108 is configured as an ultrasound receiver, it can serve as the same function as the hydrophone 1104. When it is configured as an ultrasound transmitter, the generated ultrasound signal can be received by external sensors for tracking and imaging purposes. When it is configured as both a transmitter and a receiver, it can be configured as an active reflector.

The catheter 1102 can include a channel 1110 for other catheters or tools. The embodiments of the invention are not limited to a catheter having all of the sub-component 1104-1110; one or multiple sub-components 1104-1110 can be implemented inside the catheter.

The virtual rigid body optical tracking system 1100 according to some embodiments of the invention can include a photoacoustic (PA) sensitive sheet 1112. The PA sensitive sheet 1112 can be a patch stuck to the patient's skin, or a layer of gel applied uniformly on the skin. The bottom surface of this sheet can have good acoustic coupling with the skin. The top surface of the sheet can have a strong photoacoustic effect under pulsed laser illumination. The PA sheet 1112 can be applied on top of the region of interest. During an operation, one or multiple pulsed laser beams can be sent to the PA sheet 1112. The generated PA signal propagates through the skin and can be detected by the ultrasound element 1108 on the catheter 1102. From the recorded acoustic signal time delay of laser spots at different locations, the catheter position can be calculated. In the PA sensitive sheet 1102, a giant photoacoustic effect 1114 [14] may also be implemented to improve the acoustic signal amplitude. Different from the conventional PA signal, which is generated from the target material's thermal expansion under laser illumination, a giant PA signal is generated through the target phase change effect. A material with strong giant PA effect can be used to make the PA sensitive sheet 1112.

The virtual rigid body optical tracking system 1100 according to some embodiments of the invention can include an optical tracking system 1116. The optical tracking system 1116 can be a system that is capable of acquiring camera images of the observed scene and determining the three-dimensional position of any observed point in the images. The optical tracking system 1116 can be a stereocamera system. There are many possible realizations of the optical tracking system 1116, including, but not limited to a single tracked camera, multiple camera registered together, a single camera with a structured light projector. The optical tracking system 1116 allows for the observed surface to be digitized to properly project a visualization 1118 onto the surface using a projector 1120. It also enables tracking with a virtual rigid body.

The projector 1120 can project light onto a surface. This functionality enables the visualization 1118, as well as structured light setups of the optical tracking system 1116. The visualization 1118 is a projection of guidance information onto the surface. This can include the venous structure of the patient, the location of the catheter, and other organs. The visualization 1118 can be projected by the projector 1120, and its contents can depend on the information obtained by the optical tracking system 1116, the ultrasound transduce 1122 and related components, and the catheter 1102 and related components. A possible visualization may only display pertinent information, for example, structures local to the position of the tracked catheter tip.

The virtual rigid body optical tracking system 1100 according to some embodiments of the invention can include a virtual rigid body generator 1124, and an ultrasound transducer 1122. The virtual rigid body generator 1124 can project a virtual rigid body 1126 that forms a pattern of light 1128 on a surface. The ultrasound transducer 1122 enables real-time interoperative imaging. Since it can be tracked using the virtual rigid body generator 1124 using the methods described herein, the virtual rigid body 1126, and the optical detection system 1116, the images obtained from the ultrasound transducer 1122 can be used to update any pre-operative plans. This information can also be used to update the visualization pattern 1118 projected by the projector 1120.

The virtual rigid body optical tracking system 1100 according to some embodiments of the invention can include a photoacoustic spot generator (not shown). The photoacoustic spot generator can project multiple spots or an arbitrary pattern of pulsed laser light onto a surface. Pulsed laser diodes or a fiber-coupled Nd:YAG pulsed laser system can be used to project multiple photoacoustic spots [15]. Optical gratings can be used to generate an arbitrary pattern of pulsed laser light. The photoacoustic spot generator can be separate from or attached to the ultrasound transduce 1122. According to some embodiments of the invention, the virtual rigid body generator 1124 and the photoacoustic spot generator are the same device, as shown in FIG. 11.

The photoacoustic laser points are spots of laser light generated by the photoacoustic spot generator. Each spot of pulsed laser light can generate an acoustic signal due to the photoacoustic effect. These acoustic signals can be detected by the hydrophone 1104. The hydrophone 1104 can be configured to differentiate between each of the acoustic signals. To accomplish this, the photoacoustic laser points can be projected sequentially. Another option is coding each photoacoustic laser point with intensity or wavelength. The detected acoustic signals can be used to localize the hydrophone 1104. According to some embodiments of the invention, the photoacoustic laser points can be generated in the same region as the pattern of light 1128 formed by the virtual rigid body 1126. The virtual rigid body is used simultaneously to generate photoacoustic signals. The same pattern can be used as photoacoustic points and VRB points. According to some embodiments of the invention, the virtual rigid body 1126 is used simultaneously to generate photoacoustic signals, and the same pattern 1128 can be used as photoacoustic points and VRB points.

Not all of the features described with respect to FIG. 11 are required for all embodiments of the invention, and some embodiments may have a subset of these features. For example, the virtual rigid body optical tracking system 1100 according to some embodiments of the invention can include a catheter 1102 with a hydrophone 1104, ultrasound element 1108, and a catheter 1110. The ultrasound element 1108 may function as an active echo. The virtual rigid body optical tracking system 1100 may further include an optical detection system 1116, a projector 1120, and a visualization 1118. The virtual rigid body optical tracking system 1100 may further include a VRB generator 1124, an ultrasound transducer 1122, and a virtual rigid body 1126.

As a second example, the virtual rigid body optical tracking system 1100 according to some embodiments of the invention can include a catheter 1102 with a hydrophone 1104, a PA fiber 1106, an ultrasound element 1108, and a catheter 1110. The virtual rigid body optical tracking system 1100 may further include a PA sensitive sheet 1112 and a giant PA effect. The virtual rigid body optical tracking system 1100 may further include an optical detection system 1116, a projector 1120, and a visualization 1118. The virtual rigid body optical tracking system 1100 may further include a VRB generator 1124, a virtual rigid body 1126, a PA spot generator, and PA laser points. During a catheter insertion procedure, one or multiple pulsed laser spots are projected to on the patient's skin or the PA sensitive sheet 1112 on top of the skin. Photoacoustic pulses are generated and propagate in the tissue. The ultrasound element 1108 integrated within the catheter 1102 can continuously monitor the photoacoustic pulses, so that the relative distance between the ultrasound element 1108 and the laser spots can be derived.

Figure 12:
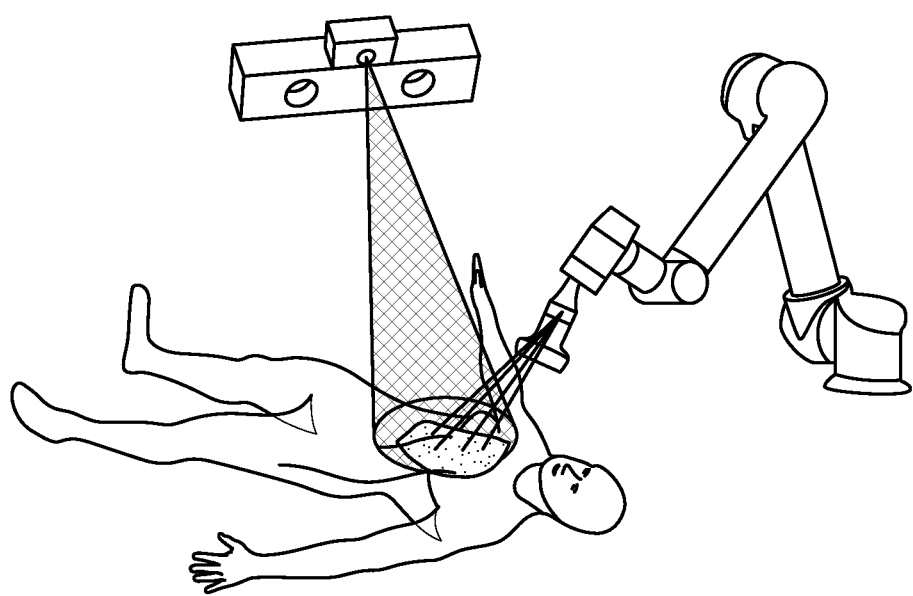
FIG. 12 shows a virtual rigid body optical tracking system with a single optical detection system, wherein a robot arm is used to hold the ultrasound transducer.

According to some embodiments of the invention, when the catheter 1102 moves, a motorized system, such as a robotic arm, can move the PA spot generator to maintain the relative distance between the ultrasound element 1108 and the spots. The robot arm can move the PA spot generator with the catheter 1102 automatically. This can be used for tracking the catheter 1102 and projecting the visualization 1118. FIG. 12 shows a virtual rigid body optical tracking system with a single optical detection system, wherein a robot arm is used to hold the ultrasound transducer. The robot arm may be controlled cooperatively, or can move autonomously. In the cooperative control paradigm, the operator and the robot both hold and share control of the surgical instrument. The force exerted by the operator guides the robot to comply with the operator's movement. According to some embodiment, the robot arm automatically maintains a distance between the PA spot generators and the catheter 1102. The camera can detect the VRB and laser spots on the patient's chest (or the PA sensitive sheet 1112) and can create a virtual fixture constraint to prevent the robot from moving to places where the laser spots are directed to the wrong surface area. Virtual fixtures are known robotic control methods in the robotic field. There are many servoing techniques based on both visual servoing [16] and ultrasound servoing [17] to enable this behavior.

An inverse virtual rigid body system and method according to some embodiments of the invention is now described. The inverse virtual rigid body is one where the tracked marker is a light sensor that detects light from an external light source. Both versions of the virtual rigid body use the same core algorithm. An inverse virtual rigid body system according to some embodiments of the invention includes one or more photodiodes. The photodiodes can be either wired or wireless for a receiver to read the photodiode signal at any timestamp. The equations and concepts described above with respect to virtual rigid body tracking can be applied to inverse virtual rigid body tracking, as will be evident to one of ordinary skill in the art.

An inverse virtual rigid body system according to some embodiments of the invention includes one or more scanning light sources for scanning an area in which an operator utilizes a tool to be tracked. The scanning light source can be a laser scanner, a laser diode, or a laser projector, for example. The scanning light source projects a collimated laser beam within a certain solid angle. The projection orientation can be rapidly changed and can scan the entire work area. The orientation of the laser beam can be recorded at any time or synchronized to an external control signal. The scanning light source and the photodiodes can be synchronized such that the signal received from the photodiode at a timestamp have a corresponding projection ray at the same timestamp. If more than one scanning light source is used, the scanning light sources can be registered together via a calibration step similar to camera calibration. [18]

The general idea is that each pair of a scanning light source and a photodiode will result in a line in the scanning light source's coordinate system that the photodiode may lie on with respect to the scanning light source. This results from the projection ray with the highest corresponding photodiode intensity. The following apparatus use variations on this idea to recover the position and orientation of a set of photodiodes attached to any tool. The inverse VRB pose can be measured in several ways. According to some embodiments of the invention, the photodiodes detect the rays from the projector source and in this case the pose can be recovered if more information is known about the geometry of these photodiodes—for example, they are all placed on a planar surface or have a unique shape. It is important to note that a camera or a stereo-camera attached to the projector source can detect the shape of the photodiodes. In this case if we have three photodiodes the pose is not uniquely identified as described in the above mathematical proof for the VRB. According to some embodiments of the invention, if photodiodes provide a time-of-flight capability through synchronization with the projector, or if the projector can detect the distance to a photodiode reflector through an interferometer approach, then the inverse VRB can detect the rays and the end positions of these rays, and hence three photodiodes are sufficient to create a unique pose of the configuration. Finally, a single photodiode (without an interferometer approach or a time-of-flight measurement) can be uniquely identified in the 3D space by have two stereo-projector or light sources where two independent rays can intersect in this single photodiode.

Figure 13:
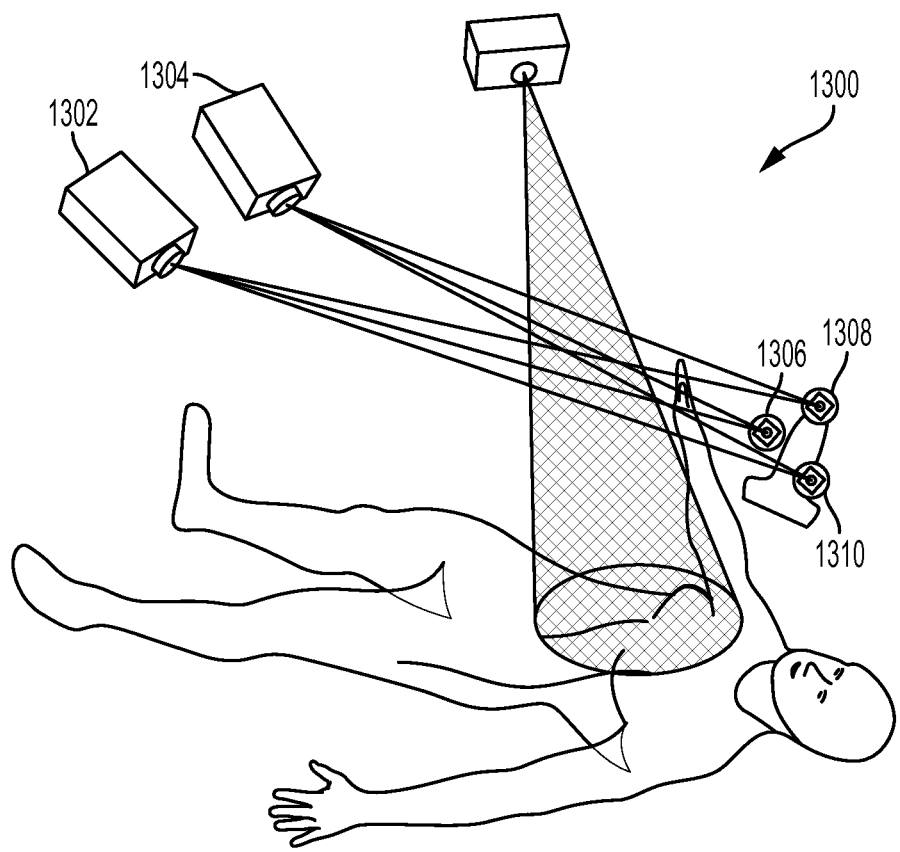
FIG. 13 shows an inverse virtual rigid body system comprising two scanning light sources and three photodiodes.

Two or more scanning light sources and their corresponding signals from a photodiode provide one or more lines each respectively in the scanning light source's coordinate system. By using the calibration information between the two or more projectors, these lines can be transformed into a single coordinate system. All of these lines will intersect at the position of the photodiode, thus uniquely define the position of the photodiode in this new coordinate system. By using three or more photodiodes, one can define a plane in this coordinate system and recover the orientation of the set of photodiodes, and thus the orientation of a tool to which the photodiodes are fixed. FIG. 13 shows an inverse virtual rigid body system 1300 comprising two scanning light sources 1302, 1304 and three photodiodes 1306-1310.

Figure 14:
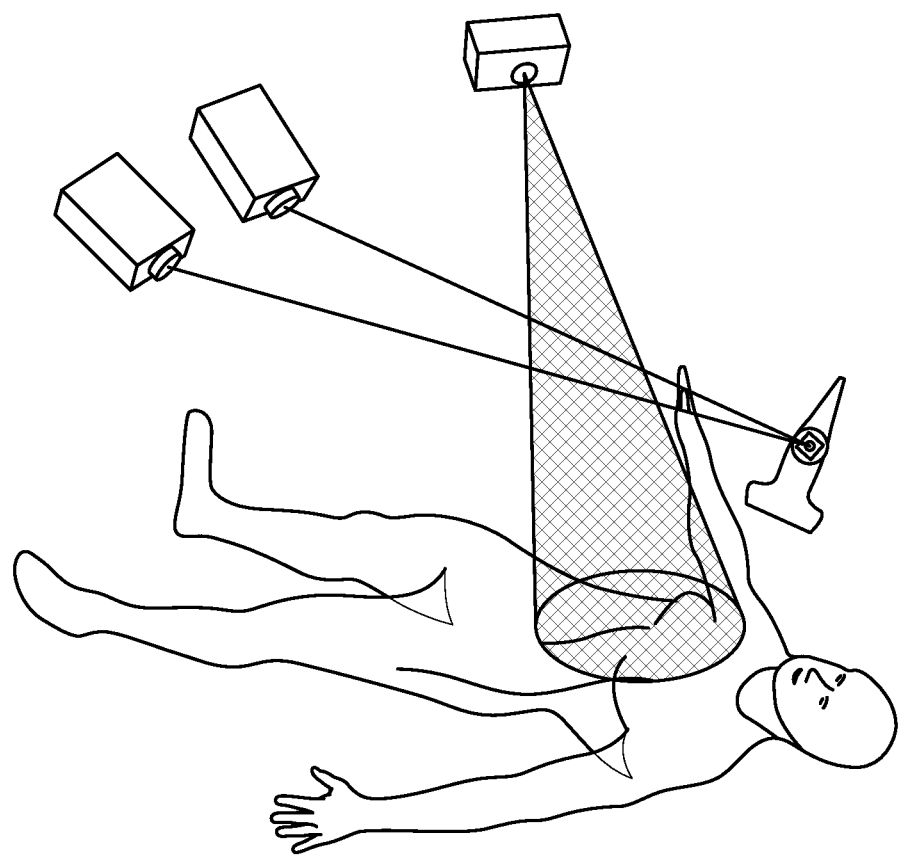
FIG. 14 shows an inverse virtual rigid body system comprising one tracked scanning light source and three photodiodes.

FIG. 14 shows an inverse virtual rigid body system comprising one tracked scanning light source and three photodiodes. By tracking the scanning light source, one can use the single scanning light source as multiple projectors. The tracking information replaces the registration between scanning light sources when multiple projectors are used. The rest follows the case of two or more projectors and three or more photodiodes.

Figure 15:
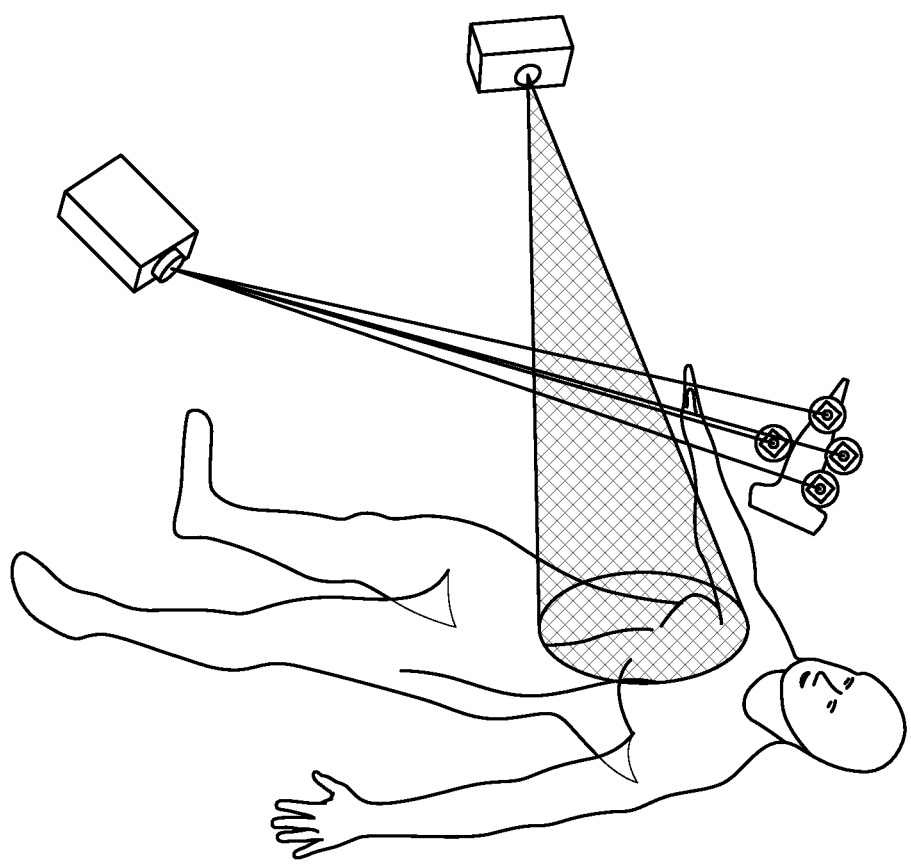
FIG. 15 shows an inverse virtual rigid body system comprising one scanning light source and three photodiodes.

FIG. 15 shows an inverse virtual rigid body system comprising one scanning light source and three photodiodes. According to some embodiments, the scanning light source is installed at a fixed location in the operation room. The scanner projection area covers the entire working area in which the operator utilize the tool to be tracked. The scanner can have a clear line of sight with the tool. Three or more photodiodes are mounted on the tool surface without lining up along a straight line. When the system operates, the scanning light source scans the work area. Once a photodiode receives the laser illumination, the orientation of the scanning beam will be recorded. Given the pre-calibrated spatial registration between the 3 photodiodes and the tool, the tool's pose and localization can be derived from the three beam orientation records which indicate the laser beam scans over the three photodiodes. Compared to the conventional optical tracker, the photodiodes measure the laser beam in an analog way, and the localization accuracy can be higher than the optical tracking.

Similar to the configuration with one scanning light source and three or more photodiodes, an inverse virtual rigid body system according to some embodiments of the invention can include one scanning light source and three or more active light reflectors. The laser beam reception information can be sent out by lighting up the LEDs instead of through an electrical wire. According to some embodiments, the inverse VRB optical tracking system can be completely wireless. An LED can be positioned next to the photodiode, and can be controlled with a circuit that enables the LED to blink or turn on once the projected ray intersects with the photodiode. In this case the system can be wireless; however, a camera is needed to detect the light from the LED. This approach can be termed optical active echo.

Similar to the configuration with one laser scanner and three or more photodiodes, an inverse virtual rigid body system according to some embodiments of the invention can include a digital projector as the scanning light source. The projection synchronization can be done by varying the projection images.

In the configurations using a single scanning light source, more than one scanning light source can be implemented in the system. There are two benefits of using multiple scanning light sources. First, it reduced the chance of the line of sight being blocked. The tracking system remains functional as long as one of the scanning light sources has clear line of sight. Second, when localizing the target through multiple scanning light sources, the light source has a large distance, which makes the triangulation more accurate.

The distance between the scanning light source and the reception photodiode can be derived from the received signal profile. Given a known scanning angular speed and the laser beam width, a longer source to target distance results in a higher line speed, thus a shorter electrical pulse from the photodiode. Similarly, the scanning light source can also have two output beams with a certain spacing. The distance measurement can be derived from the time delay between the two pulses from the two laser beams. The two laser beams can be parallel or at an angle.

REFERENCES

1. Maurer Jr. C. R., J. B. West, "Designing Optically Tracked Instruments for Image-Guided Surgery," IEEE TMI 23(5), pp. 533-545, 2004.
2. Boctor E. M., A. Viswanathan, M. A. Choti, R. H. Taylor, G. Fichtinger, G. D. Hager, "A Novel Closed Form Solution for Ultrasound Calibration," IEEE Symposium On Biomedical Imaging, pp. 427-530, 2004.
3. Scharstein D., Szeliski R., "High-Accuracy Stereo Depth Maps Using Structured Light," IEEE Proceedings of Computer Vision and Pattern Recognition, pp. 195-202, 2003.
4. Salvi J., Pages J., Batlle J., "Pattern codification strategies in structured light systems," Pattern Recognition, 37(4), pp. 827-849, 2004.
5. McIlroy P., S. Izadi, A. Fitzgibbon, "Kinectrack: Agile 6-DoF Tracking Using a Projected Dot Pattern," IEEE International Symposium on Mixed and Augmented Reality, pp. 23-29, 2012.
6. Wienss C., I. Nikitin, G. Goebbels, K. Troche, "Sceptre: an infrared laser tracking system for virtual environments," Proceedings ACM Symposium on Virtual Reality Software and Tech-nology, 2006.
7. Liu J., Gao X., Z. Zhang, S. Gao, and J. Zhou, "A New Calibration method in 3D Ultrasonic Imaging System," IEEE Engineering in Medicine and Biology Society, Vol. 20(2), pp. 839-841, 1998.
8. Byrd, R. H., R. B. Schnabel, and G. A. Shultz, "Approximate Solution of the Trust Region Problem by Minimization over Two-Dimensional Subspaces," Mathematical Programming, Vol. 40, pp 247263, 1988.
9. Levenberg, K., "A Method for the Solution of Certain Problems in Least Squares," Quart. Appl. Math. Vol. 2, pp 164168, 1944.
10. Marquardt, D., "An Algorithm for Least-Squares Estimation of Nonlinear Parameters," SIAM J. Appl. Math. Vol. 11, pp 431441, 1963.
11. Arun, K. S., T. S. Huang, and S. D. Blostein, "Least-Squares Fitting of Two 3-D Point Sets," IEEE Trans. PAMI Vol. 9(5), pp 698-700, 1987.

12. Horn, B. K. P., "Closed-form solution of absolute orientation using unit quaternions," Journal of the Optical Society of America Vol. 4, pp 629-642, 1987.

13. Hartley R. I., and P. Sturm, "Triangulation," Computer Vision and Image Understanding Vol. 68(2), pp. 146-157, 1997.

14. Guo X., "Integrated Active Ultrasound Systems for Medical Interventions," Thesis. Johns Hopkins University, 2015.

15. Cheng A., Guo X., Kang H. J., Tavakoli B., Kang J. U., Taylor R. H., and E. M. Boctor, "Concurrent photoacoustic markers for direct three-dimensional ultrasound to video registration," Proc. SPIE 8943, Photons Plus Ultrasound: Imaging and Sensing 2014, 89435J, 2014.

16. Espiau B., Chaumette F., and P. Rives, "A new approach to visual servoing in robotics," IEEE Trans. On Robotics and Automation Vol. 8(3), pp. 313-326, 1992.

17. Krupa A., Fichtinger G., and G. D. Hager, "Real-time Motion Stabilization with B-mode Ultrasound Using Image Speckle Information and Visual Servoing," The International Journal of Robotics Research Vol. 28(10), pp. 1334-1354, 2009.

18. Zhang Z., "A flexible new technique for camera calibration," IEEE Trans. On Pattern Analysis and Machine Intelligence Vol. 22(11), pp. 1330-1334, 2000.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A virtual rigid body optical tracking system for tracking a catheter in a patient, comprising:
a virtual rigid body generator configured to project a virtual rigid body,
the virtual rigid body forming a pattern of light on a surface of the patient,
the virtual rigid body generator projecting beams of light,
the beams of light forming a projection pyramid,
the projection pyramid including an apex,
the virtual rigid body generator being a photoacoustic spot generator,
the photoacoustic spot generator generating acoustic signals through a photoacoustic effect;
an optical detection system configured to detect the pattern of light; and
a data processing system in communication with the optical detection system,
the data processing system including a data processor configured to:
receive images of the pattern of light,
the images being received from the optical detection system; determine a three-dimensional position of a plurality of points,
the plurality of points including intersection points where the pattern of light intersects the surface of the patient,
the plurality of points being determined in a coordinate system of the optical detection system;
determine a corresponding position of the plurality of points in a coordinate system of the projection pyramid,
the apex being set as an origin of the coordinate system of the projection pyramid;
determine a rigid body transformation between the corresponding position of the plurality of points in the coordinate system of the projection pyramid and the three-dimensional position of the plurality of points in the coordinate system of the optical detection system;
determine a pose of the apex of the projection pyramid in the coordinate system of the optical detection system based upon the rigid body transformation,
the pose of the apex of the projection pyramid corresponding to a pose of the virtual rigid body generator;
track the virtual rigid body based upon determining the pose of the virtual rigid body generator;
determine a time delay of each acoustic signal of the acoustic signals of the photoacoustic spot generator,
the acoustic signals being received by an ultrasound element positioned on the catheter;
determine a position of the catheter based upon the time delay; and
track the catheter based upon determining the position of the catheter.

2. The virtual rigid body optical tracking system according to claim 1, where:
the virtual rigid body generator is attached to a tool, and
the data processing system is configured to determine a position of the tool based on the detected pattern of light.

3. The virtual rigid body optical tracking system according to claim 2, where the data processing system is further configured to determine an orientation of the tool based on the detected pattern of light.

4. The virtual rigid body optical tracking system according to claim 1, where the virtual rigid body generator comprises a plurality of laser diodes.

5. The virtual rigid body optical tracking system according to claim 4, where each of the plurality of laser diodes emits light at a different wavelength.

6. The virtual rigid body optical tracking system according to claim 4, where each of the plurality of laser diodes emits light with a different time modulation.

7. The virtual rigid body optical tracking system according to claim 1, where the surface of the patient comprises a region of interest.

8. The virtual rigid body optical tracking system according to claim 1, where the optical detection system is a stereocamera system.

9. The virtual rigid body optical tracking system according to claim 1, further comprising:
a second virtual rigid body generator configured to project a second virtual rigid body,
the second virtual rigid body generator projecting a second pattern of light on the surface of the patient,
the optical detection system being configured to detect the second pattern of light, and the data processing system to determine a position of the second virtual rigid body generator based on the detected second pattern of light.

10. The virtual rigid body optical tracking system according to claim 9, the second virtual rigid body generator is attached to a second tool, and
the data processing system to determine a position of the second tool based on the detected second pattern of light.

11. The virtual rigid body optical tracking system of claim 1, where the surface of the patient is one of:
a skin of the patient; or
a photoacoustic sensitive sheet disposed on the skin of the patient.

12. A virtual rigid body optical tracking system for tracking a catheter in a patient, comprising:
a virtual rigid body generator configured to project a virtual rigid body,
the virtual rigid body forming a pattern of light on a surface of the patient,
the virtual rigid body generator projecting beams of light,
the beams of light forming a projection pyramid,
the projection pyramid including an apex,
the virtual rigid body generator being a photoacoustic spot generator,
the photoacoustic spot generator generating acoustic signals through a photoacoustic effect;
an optical detection system configured to detect the pattern of light; and
a data processing system in communication with the optical detection system,
the data processing system including a data processor configured to:
receive images of the pattern of light from the optical detection system;
determine a three-dimensional position of a plurality of points,
the plurality of points including intersection points where the pattern of light intersects the surface of the patient,
the plurality of points being determined in a coordinate system of the optical detection system;
determine a corresponding position of the plurality of points in a coordinate system of the projection pyramid,
the apex being set as an origin of the coordinate system of the projection pyramid;
determine a rigid body transformation between the corresponding position of the plurality of points in the coordinate system of the projection pyramid and the three-dimensional position of the plurality of points in the coordinate system of the optical detection system;
determine a pose of the apex of the projection pyramid in the coordinate system of the optical detection system based upon the rigid body transformation,
the pose of the apex of the projection pyramid corresponding to a pose of the virtual rigid body generator;
track the virtual rigid body based upon determining the pose of the virtual rigid body generator;
determine a time delay of each acoustic signal of the acoustic signals of the photoacoustic spot generator,
the acoustic signals being received by an ultrasound element positioned on the catheter, and
determine a position of the catheter based upon the time delay.

13. The virtual rigid body optical tracking system of claim 12, where the surface is one of:
a skin of the patient; or
a photoacoustic sensitive sheet disposed on the skin of the patient.

14. The virtual rigid body optical tracking system of claim 12, where the beams of light are projected sequentially.

15. The virtual rigid body optical tracking system of claim 12, where the optical detection system is a stereocamera system.

16. A virtual rigid body optical tracking system for tracking a medical tool, comprising:
a virtual rigid body generator configured to project a virtual rigid body,
the virtual rigid body forming a pattern of light on a surface of a patient,
the virtual rigid body projecting beams of light,
the beams of light forming a projection pyramid,
the projection pyramid including an apex,
the virtual rigid body generator being a photoacoustic spot generator,
the photoacoustic spot generator generating acoustic signals through a photoacoustic effect;
a stereo camera configured to detect the pattern of light; and
a data processing system in communication with the stereo camera,
the data processing system including a data processor configured to:
receive images of the pattern of light,
the images being received from the stereo camera;
determine a three-dimensional position of a plurality of points,
the plurality of points including intersection points where the pattern of light intersects the surface of the patient,
the plurality of points being determined in a coordinate system of the stereo camera;
determine a corresponding position of the plurality of points in a coordinate system of the projection pyramid,
the apex being set as an origin of the coordinate system of the projection pyramid;
determine a rigid body transformation between the corresponding position of the plurality of points in the coordinate system of the projection pyramid and the three-dimensional position of the plurality of points in the coordinate system of the stereo camera;
determine a pose of the apex of the projection pyramid in the coordinate system of the stereo camera based upon the rigid body transformation,
the pose of the apex of the projection pyramid corresponding to a pose of the virtual rigid body generator;
track the virtual rigid body based upon determining the pose of the virtual rigid body generator;
determine a time delay of each acoustic signal of the acoustic signals of the photoacoustic spot generator,
the acoustic signals being received by an ultrasound element positioned on the medical tool;

determine a position of the medical tool based upon the time delay; and track the medical tool based upon determining the position of the medical tool.

17. The virtual rigid body optical tracking system of claim 16, where the virtual rigid body generator comprises a plurality of laser diodes.

18. The virtual rigid body optical tracking system of claim 17, where the plurality of laser diodes emit light at a different wavelength.

19. The virtual rigid body optical tracking system of claim 16, where the virtual rigid body generator comprises a projector.

20. The virtual rigid body optical tracking system of claim 16, where the virtual rigid body generator comprises a light emitting diode.

* * * * *

UNITED STATES PATENT AND TRADEMARK OFFICE
CERTIFICATE OF CORRECTION

PATENT NO. : 10,105,186 B2
APPLICATION NO. : 14/734778
DATED : October 23, 2018
INVENTOR(S) : Alexis Cheng et al.

Page 1 of 1

It is certified that error appears in the above-identified patent and that said Letters Patent is hereby corrected as shown below:

In the Specification

Column 1, Lines 7-12, change "This invention was made with U.S. Government support under grant IIS-1162095, awarded by the National Science Foundation; and grant EB015638, awarded by the Department of Health and Human Services, the National Institutes of Health (NIH). The U.S. Government has certain rights in the invention." to -- This invention was made with government support under EB015638, awarded by the National Institutes of Health. The government has certain rights in the invention. --

Signed and Sealed this
Fifteenth Day of September, 2020

Andrei Iancu
*Director of the United States Patent and Trademark Office*